US006365187B2

(12) United States Patent
Mathiowitz et al.

(10) Patent No.: US 6,365,187 B2
(45) Date of Patent: \*Apr. 2, 2002

(54) BIOADHESIVE MICROSPHERES AND THEIR USE AS DRUG DELIVERY AND IMAGING SYSTEMS

(75) Inventors: Edith Mathiowitz, Brookline; Donald E. Chickering, III, Framingham; Jules Serge Jacob, Tauton, all of MA (US)

(73) Assignee: Brown University Research Foundation, Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/773,229

(22) Filed: Jan. 31, 2001

Related U.S. Application Data

(63) Continuation of application No. 08/824,172, filed on Mar. 26, 1997, now Pat. No. 6,235,313, which is a continuation-in-part of application No. 08/052,473, filed on Apr. 23, 1993, now Pat. No. 6,217,908, which is a continuation-in-part of application No. 07/873,480, filed on Apr. 24, 1992, now Pat. No. 6,197,346.

(51) Int. Cl.[7] .................................................. A61K 9/14
(52) U.S. Cl. ........................ 424/486; 424/484; 424/489; 424/491; 514/962; 514/772.6
(58) Field of Search .............................. 424/486, 484, 424/489, 491, 490, 493, 9.1, 9.32, 9.4; 514/962, 772.6, 963, 964, 965

(56) References Cited

U.S. PATENT DOCUMENTS

| | | | |
|---|---|---|---|
| 4,795,436 A | 1/1989 | Robinson | 424/422 |
| 4,818,542 A | 4/1989 | DeLuca et al. | 424/491 |
| 4,839,416 A | 6/1989 | Orenstein et al. | 524/558 |
| 4,959,219 A | 9/1990 | Chow et al. | 424/495 |
| 4,976,968 A | 12/1990 | Steiner | 424/491 |

(List continued on next page.)

FOREIGN PATENT DOCUMENTS

| | | |
|---|---|---|
| EP | 0 333 523 | 9/1989 |
| WO | WO 90/06430 | 5/1991 |
| WO | WO 90/06433 | 5/1991 |
| WO | WO 91/06286 | 5/1991 |
| WO | WO 91/06287 | 5/1991 |

OTHER PUBLICATIONS

Allen, et al., "Mucus Glycoprotein Structure, Gel Formation and Gastrointestinal Mucus Function" in *Mucus and Mucosa, Ciba Foundation Symposium 109* (Nugent & O'Connor, eds.) p. 137 (London 1984).

Beck, et al., "A New Long–acting Injectable Microcapsule System for the Administration of Progesterone," *Fertil. & Steril.*, 31(5):545–55 (1979).

Benita, et al., "Characterization of Drug–Loaded Poly(d,/– lactide) Microspheres," *J. Pharm. Sci.* 73(12):1721–24 (1984).

(List continued on next page.)

*Primary Examiner*—Thurman K. Page
*Assistant Examiner*—Lakshimi Channavajjala
(74) *Attorney, Agent, or Firm*—Holland & Knight LLP

(57) ABSTRACT

Bioadhesive polymers in the form of, or as a coating on, microcapsules containing drugs or bioactive substances which may serve for therapeutic, or diagnostic purposes in diseases of the gastrointestinal tract, are described. The polymeric microspheres all have a bioadhesive force of at least 11 mN/cm$^2$ (110 N/m$^2$) Techniques for the fabrication of bioadhesive microspheres, as well as a method for measuring bioadhesive forces between microspheres and selected segments of the gastrointestinal tract in vitro are also described. This quantitative method provides a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical consideration, should be used for making bioadhesive microspheres.

23 Claims, 7 Drawing Sheets

U.S. PATENT DOCUMENTS

| | | | | |
|---|---|---|---|---|
| 5,069,936 | A | | 12/1991 | Yen .............................. 424/491 |
| 5,200,181 | A | | 4/1993 | Soltys et al. ................. 424/489 |
| 5,240,963 | A | | 8/1993 | Domb et al. ............. 514/772.6 |
| 5,403,750 | A | | 4/1995 | Braetz et al. ................ 436/531 |
| 5,543,158 | A | | 8/1996 | Gref et al. ................... 424/501 |
| 5,686,113 | A | | 11/1997 | Speaker et al. .............. 424/490 |
| 5,744,155 | A | | 4/1998 | Friedman et al. ............ 424/434 |
| 5,879,712 | A | | 3/1999 | Bomberger et al. ......... 424/489 |
| 5,942,252 | A | | 8/1999 | Tice et al. ................... 424/501 |
| 6,217,908 | B1 | * | 4/2001 | Mathiowitz et al. ........ 424/493 |
| 6,235,313 | B1 | * | 5/2001 | Mathiowitz et al. ........ 424/486 |
| 6,197,346 | B1 | * | 6/2001 | Mathiowitz et al. ........ 424/493 |

OTHER PUBLICATIONS

Chickering & Mathiowitz, "Bioadhesive microspheres: i. A novel electrobalance–based method to study adhesive interactions between individual microspheres and intestinal mucosa," *J. Control. Release* 34:251–62 (1995).

Ch'ng, et al., "Bioadhesive Polymers as Platforms for Oral Controlled Drug Delivery II: Synthesis and Evaluation of Some Swelling, Water–Insoluble Bioadhesive Polymers," *J. Pharm. Sci.* 74: 399–405 (1988).

Duchêne, et al., "Pharmaceutical and Medical Aspects of Bioadhesive Systems for Drug Administration," *Drug Development &. Ind. Pharm.* 14(2&3):283–31 (1988).

Gurney, et al., "Bioadhesive intraoral release systems: design, testing and analysis," *Biomaterials* 5:336–40 (1984).

Horowitz, "Mucopolysaccharides and glycoproteins of the alimentary tract," in *Handbook of Physiology* (C.F. Code, ed.), pp. 1063–1085 (American Physiological Society 1967).

Illum, "Bioadhesive Microspheres as Potential Nasal Drug Delivery System," *Int'l J. Pharm.* 39: 189–99 (1987).

Labat–Robert & Decaens, "Glycoprotéines du mucus gastrique: structure, fonctions et pathologie," *Pathologie Biologie* 24:241 (Paris 1979).

Lehr, et al., "Intestinal transit of bioadhesive microspheres in an in situ loop in the rat—a comparative study with copolymers and blends based on poly(acrylic acid)," *J. Controlled Rel.* 13:51–62 (1990).

Lehr, et al., "In vitro evaluation of mucoadhesive properties of chitosan and some other natural polymers," *International J. Pharmaceutics* 78: 43–48 (1992).

Leon–Bay, et al., "Microsphere formation and drug delivery in a series of derivatized amino acids," Winter conference of Medicinal Chemistry (Steamboat Springs, Colarodo 1995).

Mathiowitz, et al., "Morphology of polyanhydride microsphere delivery systems," *Scanning Microscopy* 4(2):329–340 (1990).

Mathiowitz, et al., "Novel microcapsules for delivery systems," *Reactive Polymers* 6:275–83 (1987).

Mikos, et al., "Interaction of Polymer Microspheres with Mucin Gels as a Means of Characterizing Polymer Retention on Mucus," *J. Colloid & Interface Sci.* 143(2):366–73 (1991).

Park, et al., "Alternative Approaches to Oral Controlled Drug Delivery: Bioadhesives and In–Situ Systems" in *Recent Advances in Drug Delivery Systems* (Anderson & Kim, eds.) pp. 163–183 (Plenum Press, New York 1984).

Pigman, et al., "Submaxillary Gland Glycoproteins" in *Glycoproteins: Their Composition, Structure and Function* (Gottschalk, ed.) pp. 434–45 (Amsterdam: Elsevier Pub. Co. 1966).

Scawen, et al., "The Action of Proteolytic Enzymes on the Glycoprotein from Pig Gastric Mucus," *Biochemical J.* 163:363–68 (1977).

Smart, et al., "An in vitro investigation of mucosa–adhesive materials for use in controlled drug delivery," *J. Pharm. & Pharmacol.* 36:295–99 (1984).

Spiro, "Glycoproteins," Annual Review of Biochemistry 39:599–638 (Snell, ed. 1970).

* cited by examiner

BIOADHESIVE MICROSPHERES AND THEIR USE AS DRUG DELIVERY AND IMAGING SYSTEMS

This is a continuation of U.S. Ser. No. 08/824,172 filed Mar. 26, 1997, U.S. Pat. No. 6,235,313, entitled "*Bioadhesive Microspheres and Their Use as Drug Delivery and Imaging Systems*", by Edith Mathiowitz, Donald E. Chickering, III, and Jules Serge Jacob, which is a continuation-in-part of U.S. Ser. No. 08/052,473 filed Apr. 23, 1993, U.S. Pat. No. 6,217,908, which is a continuation-in-part of U.S. Ser. No. 07/873,480 filed Apr. 24, 1992, U.S. Pat No. 6,197,346.

BACKGROUND OF THE INVENTION

This invention is generally in the area of drug delivery systems, especially in the area of gastrointestinal, vaginal and respiratory drug delivery.

Drug delivery takes a variety of forms, depending on the agent to be delivered and the administration route. A preferred mode of administration is non-invasive; i.e., administration via nasal or oral passages. Some compounds are not suited for such administration, however, since they are degraded by conditions in the gastrointestinal tract or do not penetrate well into the blood stream.

Controlled release systems for drug delivery are often designed to administer drugs in specific areas of the body. In the gastrointestinal tract it is critical that the drug not be entrained beyond the desired site of action and eliminated before it has had a chance to exert a topical effect or to pass into the bloodstream. If a drug delivery system can be made to adhere to the lining of the appropriate viscus, its contents will be delivered to the targeted tissue as a function of proximity and duration of the contact.

There are two major aspects to the development of an adhesive bond between a polymer and the gastrointestinal tissue: (i) the surface characteristics of the bioadhesive material, and (ii) the nature of the biological material with which the polymer comes in contact. The intestinal mucosa is formed of a continuous sheet of epithelial cells of absorptive and mucin-secreting cells. Overlying the mucosa is a discontinuous protective coating, the mucus, which is made of more than 95% water, as well as electrolytes, proteins, lipids and glycoproteins—the latter being responsible for the gel-like characteristics of the mucus. These glycoproteins consist of a protein core with covalently attached carbohydrate chains terminating in either sialic acid or L-fucose groups. The carbohydrate structure of the intestinal mucous glycoproteins is similar to that of the glycoproteins which are part of the epithelial cell membrane. The mucous glycoproteins act as "dummy receptors" for carbohydrate binding ligands which have evolved in nature to allow microorganisms and parasites to establish themselves on the gut wall. One function of the mucus is to intercept these ligands and associated ineffective agents and thereby protect the mucosa.

An orally ingested product can adhere to either the epithelial surface or the mucus. For the delivery of bioactive substances, it would be advantageous to have a polymeric device adhere to the epithelium rather than solely to the mucous layer, although mucoadhesion may also substantially improve bioavailability. For some types of imaging purposes, adhesion to both the epithelium and mucus is desirable whereas in pathological states, such as in the case of gastric ulcers or ulcerative colitis, adhesion to cells below the mucous layer may occur.

Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells.

Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 523 by The UAB Research Foundation and Southern Research Institute. EPA 0 333 523 describes microparticles of less than ten microns in diameter that contain antigens, for use in oral administration of vaccines. The microparticles are formed of polymers such as poly (lactide-co-glycolide), poly(glycolide), polyorthoesters, poly(esteramides), polyhydroxybutyric acid and polyanhydrides, and are absorbed through the Peyer's Patches in the intestine, principally as a function of size.

It would be advantageous if there was a method or means for controlling or increasing the absorption of these particles through the mucosal lining, or for delaying still further transit of the particles through the nasal or gastrointestinal passages.

Duchene, et al., *Drug Dev. Ind. Pharm.* 14(2&3), 283–318 (1988), reviews the pharmaceutical and medical aspects of bioadhesive systems for drug delivery. "Bioadhesion" is defined as the ability of a material to adhere to a biological tissue for an extended period of time. Bioadhesion is clearly one solution to the problem of inadequate residence time resulting from the stomach emptying and intestinal peristalsis, and from displacement by ciliary movement. For sufficient bioadhesion to occur, an intimate contact must exist between the bioadhesive and the receptor tissue, the bioadhesive must penetrate into the crevice of the tissue surface and/or mucus, and mechanical, electrostatic, or chemical bonds must form. Bioadhesive properties of the polymers is affected by both the nature of the polymer and by the nature of the surrounding media.

Duchene, et al., tested polymers for bioadhesion by measuring the surface tension between a plate containing a mucus sample and a polymer coated glass plate. They review other systems using intestinal membrane rather than a mucosal solution, and in vivo studies using rats and radiolabeled polymeric material in a gelatin capsule. A number of polymers were characterized as to their bioadhesive properties but primarily in terms of "excellent" or "poor". Polycarbophils and acrylic acid polymers were noted as having the best adhesive properties, although the highest adhesive forces were still less than 11 mN/cm$^2$.

Others have explored the use of bioadhesive polymers. Smart, et al., *J. Pharm. Pharmacol.* 36:295–299 (1984), reported on a method to test adhesion to mucosa using a polymer coated glass plate contacting a dish of mucosa. A variety of polymeric materials were tested, including sodium alginate, sodium carboxymethylcellulose, gelatin, pectin, and polyvinylpyrrolidone. Gurney, et al., *Biomaterials* 5, 336–340 (1984), concluded that adhesion may be effected by physical or mechanical bonds; secondary chemical bonds;

and/or primary, ionic or covalent bonds. Park, et al., *Alternative Approaches to Oral Controlled Drug Delivery: Bioadhesives and In-Situ Systems* 163–183 J. M. Anderson and S. W. Kim, ed., *Recent Advances in Drug Delivery* (Plenum Press NY 1984), reported on the use of fluorescent probes in cells to determine adhesiveness of polymers to mucin/epithelial surfaces. Their results indicated that anionic polymers with high charge density appear to be preferred as adhesive polymers.

None of these studies involved the study of tensile measurement between microspheres and intestinal tissue. Microspheres will be affected by other factors, such as the mucosal flow, peristaltic motion, high surface area to volume ratio, Mikos, et al., in *J. Colloid Interface Sci.* 143, 2:366–373 (May 1991) and Lehr, et al., *J. Controlled Rel. Soc.* 13:51–62 (1990), both disclose the bioadhesive properties of polymers used for drug delivery: polyanhydrides and polyacrylic acid, respectively. Mikos, et al., report that the bioadhesive forces are a function of surface area, and are significant only for particles in excess of 900 microns in diameter (having a maximum adhesive force of 120 $\mu$N for a sphere with a diameter of approximately 1200$\mu$, equivalent to 10.9 mN/cm$^2$), when measured in vitro. However, they also note that this may not be an adequate adhesive force in vivo, since the larger particle size is also subjected to greater flow conditions along the mucosa which may serve to displace these larger particles. In addition, Mikos, et al., found very small forces for particles smaller than 750$\mu$. Lehr, et al., screened two commercially available microparticles of a diameter in excess of 500 microns formed of copolymers of acrylic acid, using an in vitro system, and determined that one copolymer "Polycarbophil" increased adhesion over a control but that the other polymer did not. Polymeric coatings were also applied to polyhydroxyethylmethacrylic acid and tested in an in vivo model. As shown in Table 1 of Mikos, et al., the maximum adhesive force was approximately 9 mN/cm$^2$ for Polycarbophil.

Most prior art techniques for measuring in vitro bioadhesion are based on tensile experiments. These techniques were mainly designed for large tablets or polymer coated onto glass plates. Only a few in vitro techniques for direct measurement of adhesion forces between individual microcapsules and intestinal tissue are known. Some publications report on a flow channel method. However, the only reported results are static measurements where the mucoadhesive force exerted on each particle was determined by placing small particles over intestinal mucosa and measuring the immersed surface area and the directional contact angles using video microscopy, as described by Mikos, et al.

Many of the currently approved drugs are delivered systemically only by injection due to low bioavailability when orally administered. It would be advantageous both from cost considerations as well as patient compliance and comfort if these drugs could be administered orally, nasally, or through the pulmonary tract, using a system increasing bioavailability.

It is therefore an object of the present invention to provide drug delivery formulation that are useful for drug delivery via the mucosal membranes.

SUMMARY OF THE INVENTION

Bioadhesive polymers in the form of, or as a coating on, microcapsules containing drugs, for therapeutic purposes, are described. Preferred drugs are those which are approved by the Food & Drug Administration but which are not sufficiently bioavailable when administered orally, nasally, or through the pulmonary tract, except when encapsulated within the bioadhesive polymeric microspheres described herein. The polymeric microspheres all have a bioadhesive force of at least 11 mN/cm$^2$ (110 N/m$^2$) using the tensile measuring device described herein. Techniques for the fabrication of bioadhesive microspheres, as well as a method for measuring bioadhesive forces between microspheres and mucosa, are also described. Preferred polymers are synthetic polymers, especially copolymers of fumaric acid and sebacic acid.

BRIEF DESCRIPTION OF THE DRAWINGS

FIG. 4b is a graph of the force of detachment/surface area (mN/cm$^2$) versus microsphere diameter (microns) for p(CPP:SA) microspheres. In this figure, the values from FIG. 4a have been converted to force values and normalized by the projected surface areas as described in FIG. 3a.

FIG. 5b is a graph for force of detachment per projected surface area versus microsphere diameter for P(FA:SA) microspheres. In this figure, the values from FIG. 5a have been converted to force values and normalized by the projected surface areas as described in FIG. 3a.

DETAILED DESCRIPTION OF THE INVENTION

Figure 1:
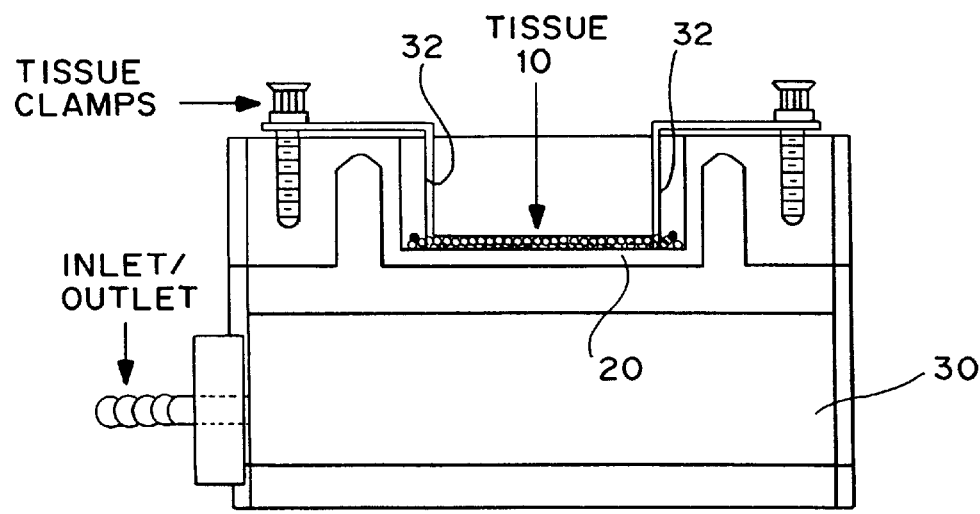
FIG. 1 is a perspective view of a tissue chamber used to measure bioadhesive forces of polymeric microspheres.

In general terms, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups responsible for forming hydrogen bonds are the hydroxyl (—OH) and the carboxylic groups (—COOH).

Adhesive polymeric microspheres have been selected on the basis of the physical and chemical bonds formed as a function of chemical composition and physical characteristics, such as surface area, as described in detail below. These microspheres are characterized by adhesive forces to mucosa of greater than 11 mN/cm$^2$. The size of these microspheres range from between a nanoparticle to a millimeter in diameter. The adhesive force is a function of polymer composition, biological substrate, particle morphology, particle geometry (e.g., diameter) and surface modification.

Classes of Polymers Useful in Forming Bioadhesive Microspheres.

Suitable polymers that can be used to form bioadhesive microspheres include soluble and insoluble, biodegradable and nonbiodegradable polymers. These can be hydrogels or thermoplastics, homopolymers, copolymers or blends, natural or synthetic. The preferred polymers are synthetic polymers, with controlled synthesis and degradation characteristics. Most preferred polymers are copolymers of fumaric acid and sebacic acid, which have unusually good bioadhesive properties when administered to the gastrointestinal.

A key requirement is that the polymer must produce a bioadhesive interaction between 110 N/m$^2$ (11 mN/cm$^2$) and 100,000 N/m$^2$ when applied to the mucosal surface of rat intestine. The forces described herein refer to measurements made upon rat intestinal mucosa, unless otherwise stated. The same adhesive measurements made on a different species of animal will differ from those obtained using rats. This difference is attributed to both compositional and geometrical variations in the mucous layers of different animal species as well as cellular variations in the mucosal epithelium. However, the data shows that the same general trends prevail no matter what animal is studied (i.e., P(FA:SA) produces stronger adhesions than PLA in rats, sheep, pigs, etc.).

The mucous layer varies from species to species and even animal to animal due to differences arising from variations in diet, location, GI activity, sex and state of health. In general, GI mucus is made of 95% water and 5% electrolytes, lipids, proteins and glycoproteins, as described by Spiro, R. G., "Glycoproteins," *Annual Review of Biochemistry*, 39, 599–638, 1970; Labat-Robert, J. & Decaeus, C., "Glycoproteins du Mucus Gastrique: Structure, Function, et Pathologie," *Pathologie et Biologie* (Paris), 24, 241 1979. However, the composition of the latter fraction can vary greatly. Proteins, including the protein core of the glycoproteins, can made up anywhere from 60 to 80% of this fraction. Horowitz, M. I., "Mucopolysaccharides and Glycoproteins of the Alimentary Tract" in *Alimentary Canal* (eds. C. F. Code), pp. 1063–1085 (Washington: American Physiological Society, 1967). The glycoproteins typically have a molecular weight of approximately two million and consist of a protein core (approximately 18.6–25.6% by weight) with covalently attached carbohydrate side chains (approximately 81.4–74.4% by weight) terminating in either L-fucose or sialic acid residues. Spiro, R. G., "Glycoproteins," *Annual Review of Biochemistry*, 39, 599–638, 1970; Scawen, M. & Allen, A., "The Action of Proteolytic Enzymes on the Glycoprotein from Pig Gastric Mucus," *Biochemical Journal*, 163, 363–368, 1977; Horowitz, M. I. & Pigman, W., *The Glycoconjugates*, pp. 560 (New York: Academic Press, Inc., 1977); Pigman, W. & Gottschalk, A., "Submaxillary Gland Glycoproteins" in *Glycoproteins: Their Composition, Structure and Function* (eds. A. Gottschalk), pp. 434–445 (Amsterdam: Elsevier Publishing Company, Inc., 1966). Species and location differences in the composition of these glycoproteins have been reported by Horowitz, M. I., "Mucopolysaccharides and Glycoproteins of the Alimentary Tract" in *Alimentary Canal* (eds. C. F. Code), pp. 1063–1085 (Washington: American Physiological Society, 1967).

In order for bioadhesive particles to embed themselves or become engulfed in the mucus lining the GI tract, the radius of the individual particles should be as thick as the thickness of the natural mucous layer. It has been shown that the gastric mucous layer thickness typically varies from 5 to 200$\mu$ in the rat and 10 to 400 $\mu$ in man. Occasionally, however, it can reach thicknesses as great as 1000$\mu$ in man, as described by Spiro, R. G., "Glycoproteins," *Annual Review of Biochemistry*, 39, 599–638, 1970; Labat-Robert, J. & Decaeus, C., "Glycoproteins du Mucus Gastrique: Structure, Fonction, et Pathologie," *Pathologie et Biologie* (Paris), 24, 241, 1979; Allen, A., Hutton, D. A., Pearson, J. P., & Sellers, L. A., "Mucus Glycoprotein Structure, Gel Formation and Gastrointestinal Mucus Function" in *Mucus and Mucosa, Ciba Foundation Symposium* 109 (eds. J. Nugent & M. O'Connor), pp. 137 (London: Pitman, 1984). Obvious physical differences in the mucus thickness were observed in the studies described herein. For example, the mucous layers in the rat and monkey were substantially thinner than those observed in the pig and sheep. Although the general order of adhesiveness was maintained throughout the studies, it must be noted that the tenacity of adhesion was dependent on the abundance of mucus.

In the past, two classes of polymers have appeared to show useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. In other studies, the most promising polymers were sodium alginate, carboxymethylcellulose, hydroxyethylcellulose and methylcellulose. Some of these materials are water-soluble, while others are hydrogels.

Rapidly bioerodible polymers such as poly[lactide-co-glycolide], polyanhydrides, and polyorthoesters, whose carboxylic groups are exposed on the external surface as their smooth surface erodes, are excellent candidates for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, and polysaccharides, such as cellulose, dextrans, polyhyaluronic acid, polymers of acrylic and methacrylic esters and alginic acid. These are not preferred due to higher levels of variability in the characteristics of the final products, as well as in degradation following administration. Synthetically modified natural polymers include alkyl celluloses, hydroxyalkyl celluloses, cellulose ethers, cellulose esters, and nitrocelluloses.

Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Other polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, and polyvinylphenol. Representative bioerodible polymers include polylactides, polyglycolides and copolymers thereof, poly (ethylene terephthalate), poly(butic acid), poly(valeric acid), poly(lactide-co-caprolactone), poly[lactide-co-glycolide], polyanhydrides, polyorthoesters, blends and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

In the studies detailed below, a variety of polymer microspheres were compared for adhesive force to mucosa. Negatively charged hydrogels, such as alginate and carboxymethylcellulose, with exposed carboxylic groups on the surface, were tested, as well as some positively-charged hydrogels, such as chitosan. The rationale behind this choice is the fact that most cell membranes are actually negatively charged and there is still no definite conclusion as to what the most important property is in obtaining good bioadhesion to the wall of the gastrointestinal tract. Thermoplastic polymers, including (a) non-erodible, neutral polystyrene, and (b) semicrystalline bioerodible polymers that reveal or generate carboxylic groups as they degrade, polylactides and polyanhydrides, were also tested. Polyanhydrides are better candidates for bioadhesive delivery systems since, as hydrolysis proceeds, causing surface erosion, more and more carboxylic groups are exposed to the external surface. However, polylactides erode more slowly by bulk erosion. In designing bioadhesive polymeric systems based on polylactides, polymers that have high concentrations of carboxylic acid are preferred. This can be accomplished by using low molecular weight polymers (Mw 2000), since low molecular weight polymers contain high concentration of carboxylic acids at the end groups.

Measurement of Bioadhesive Properties Using a Tensile Technique

The adhesive forces between polymer microspheres and segments of intestinal rat tissue can be measured using the Cahn DCA-322, as shown in FIG. 1. Although this piece of equipment is designed for measuring contact angles and surface tensions using the Wilhelmy plate technique, it is also an extremely accurate microbalance. The DCA-322 system includes a microbalance stand assembly, a Cahn DACS computer, and an Okidata Microline 320 dot matrix printer. The microbalance unit consists of stationary sample and tare loops and a moving stage powered by a stepper motor. The balance can be operated with samples weighing up to 3.0 g, and has a sensitivity rated at 0.001 dynes (10 nN). The stage speed can be adjusted from 20 to 264 $\mu$/sec using the factory installed motor, or from 2–24 $\mu$/sec using the optional slow motor. Adhesive forces were measured by attaching a polymer sample to one of the sample loops and placing an adhesive substrate 10, intestinal tissue, below it on the moving stage 20. For adhesive measurements, 1.5 cm sections are cut from the excised intestine. These were then sliced lengthwise and spread flat, exposing the lumen side. The samples were then placed in a temperature-regulated chamber 30, clamped 32 at their edges, and covered with approximately 0.9 cm high level of Dulbecco's phosphate buffered saline (DPBS, pH 7.4, osmolarity of 294 mOsm), as shown in FIG. 1. Physiologic conditions were maintained in the chamber. The chamber was then placed in the microbalance enclosure and a microsphere, mounted on a wire and hung from the sample loop of the microbalance, was brought in contact with the tissue. The microspheres were left in contact with the tissue for seven minutes with an applied force of approximately 0.25 mN and then pulled vertically away from the tissue sample while recording the required force for detachment. The contact area was estimated to be the surface area of the spherical cap defined by the depth of penetration of the bead below the surface level of the tissue.

The force values were normalized by the projected area of this cap (Area=$\pi R^2 - \pi(R-a)^2$, where R is the microsphere radius and a is the depth of penetration. For microspheres larger than 1000 μm, a=500 μm was used, for smaller microspheres a=R was used.

Figure 2:
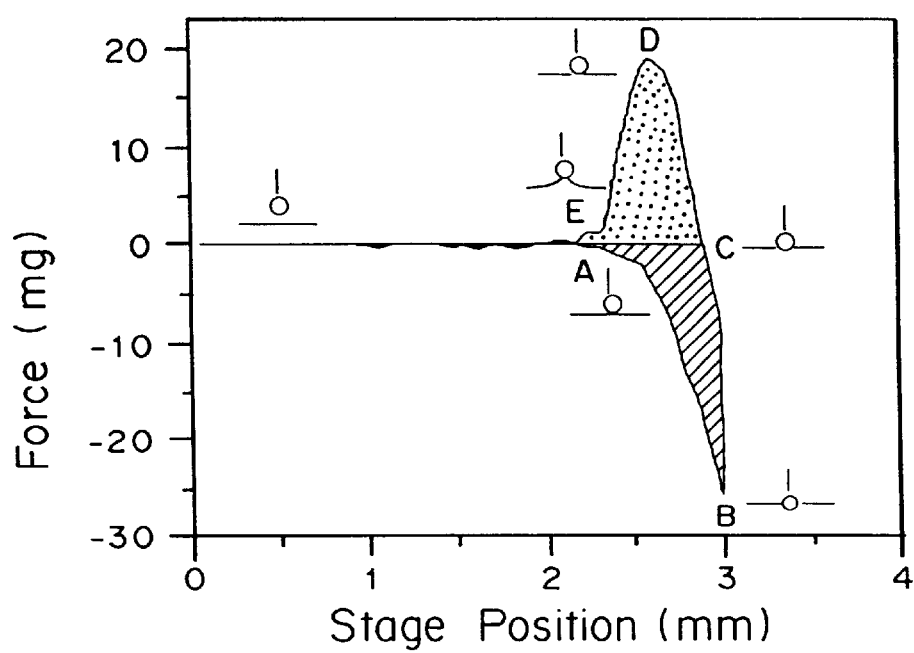
FIG. 2 is a graph of force (mg) versus stage position (mm) for a typical P(CPP:SA) microsphere.

Graphs of force versus distance as well as force versus time were studied. FIG. 2 shows a typical graph of force versus stage position for the P(CPP-SA) (20:80) microspheres. The recording starts with the microsphere suspended above the segment of tissue. The horizontal line of zero force, from position zero to point A, is the distance that the stage is raised upward before contact is made between the tissue and the microsphere. The point at which the microsphere initially makes contact with the tissue is represented by position A. Point B is the maximum applied force, which can be varied in each experiment, and which will indirectly affect the degree of penetration into the tissue. At position B the stage is held stationary in order to allow contact and formation of an adhesive bond between the microsphere and the tissue. Segment BC indicates downward motion of the stage to the point of 0 mg applied force (point C). During the early part of the tensile experiment (CD), the force increases as a function of stage position, while the contact area between the sphere and the mucus is assumed to be constant and equal to the surface of the immersed sphere. Point D represents the maximum adhesive force or "peak load". The next portion of this curve (DE) indicates a period where partial detachment of the polymeric device from the mucus occurs with some changes in the contact area. The last point (E) is the point of complete detachment of the sphere from the mucosal layer. In some cases, detachment does not occur until the microsphere has been moved to a height of 4 mm above the initial level of contact.

From these graphs it was possible to determine the maximum force applied in compression to the sample (point B), the maximum adhesive tensile force (point D), the distance that the stage moves from the initial point of contact until the motion of the stage is stopped (i.e., penetration or compressive deformation (distance BC), the distance required for complete detachment of the sample (i.e., elongation or tensile deformation (distance CE)). It was also possible to determine the compressive energy (the area bounded by AB, the horizontal axis, and the perpendicular from B to the horizontal axis), the energy loss during deformation (compressive energy minus the area bounded by BC, the horizontal axis, and the perpendicular from B to the horizontal axis) and the work of detachment or tensile energy (area CDE). Using this type of analysis, one could quantify the adhesive forces of a variety of individual microspheres and correlate these forces with physical and chemical properties of the polymers. Although the maximum adhesive force is an important factor, it may not be the sole determinant in evaluating materials for use as bioadhesives. Other useful parameters include the yield point (defined as the point at which the tensile curve deviates from linearity), the stiffness (the initial slope of the tensile curve in the linear region), and the work of detachment. Based on data on the work of detachment, both alginate and poly (fumaric-co-sebacic anhydride) are strong bioadhesives.

Modification of Polymers.

The polymers were selected from commercially available materials that could be fashioned into microsphere delivery devices or used to coat pre-existing microspheres. In some instances, the polymeric material could be modified to improve bioadhesion (to force values greater than 11 mN/cm$^2$) either before or after the fabrication of microspheres.

For example, the polymers can be modified by increasing the number of carboxylic groups accessible during biodegradation, or on the polymer surface. The polymers can also be modified by binding amino groups to the polymer. The polymers can also be modified using any of a number of different coupling chemistries that covalently attach ligand molecules with bioadhesive properties to the surface-exposed molecules of the polymeric microspheres.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9–10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1–8 and is suitable for transit through the intestine.

Any suitable coupling method known to those skilled in the art for the coupling of ligands and polymers with double bonds, including the use of UV crosslinking, may be used for attachment of bioadhesive ligands to the polymeric microspheres described herein. Any polymer that can be modified through the attachment of lectins can be used as a bioadhesive polymer for purposes of drug delivery or imaging.

Lectins that can be covalently attached to microspheres to render them target specific to the mucin and mucosal cell layer could be used as bioadhesives. Useful lectin ligands include lectins isolated from: *Abrus precatroius, Agaricus bisporus, Anguilla anguilla, Arachis hypogaea, Pandeiraea simplicifolia, Bauhinia purpurea, Caragan arobrescens, Cicer arietinum, Codiurn fragile, Datura stramonium, Dolichos biflorus, Erythrina corallodendron, Erythrina cristagalli, Euonymus europaeus, Glycine max, Helix*

*aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique,* as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius,* and *Lotus tetragonolobus.*

The attachment of any positively charged ligand, such as polyethyleneimine or polylysine, to any microsphere may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microspheres with the appropriate chemistry, such as CDI, and be expected to influence the binding of microspheres to the gut. For example, polyclonal antibodies raised against components of mucin or else intact mucin, when covalently coupled to microspheres, would provide for increased bioadhesion. Similarly, antibodies directed against specific cell surface receptors exposed on the lumenal surface of the intestinal tract would increase the residence time of beads, when coupled to microspheres using the appropriate chemistry. The ligand affinity need not be based only on electrostatic charge, but other useful physical parameters such as solubility in mucin or else specific affinity to carbohydrate groups.

The covalent attachment of any of the natural components of mucin in either pure or partially purified form to the microspheres would decrease the surface tension of the bead-gut interface and increase the solubility of the bead in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the microspheres. The polyamino chains would increase bioadhesion by means of chain entanglement in mucin strands as well as by increased carboxylic charge.

Formation of Microspheres.

As used herein, the term "microspheres" includes microparticles and microcapsules (having a core of a different material than the outer wall), having a diameter in the nanometer range up to 5 mm. The microsphere may consist entirely of bioadhesive polymer or have only an outer coating of bioadhesive polymer.

As characterized in the following examples, microspheres can be fabricated from different polymers using different methods. Polylactic acid blank microspheres were fabricated using three methods: solvent evaporation, as described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984); hot-melt microencapsulation, as described by E. Mathiowitz, et al., *Reactive Polymers*, 6, 275 (1987); and spray drying. Polyanhydrides made of bis-carboxyphenoxypropane and sebacic acid with molar ratio of 20:80 P(CPP-SA) (20:80) (Mw 20,000) were prepared by hot-melt microencapsulation. Poly(fumaric-co-sebacic) (20:80) (Mw 15,000) blank microspheres were prepared by hot-melt microencapsulation. Polystyrene microspheres were prepared by solvent evaporation.

Hydrogel microspheres were prepared by dripping a polymer solution from a reservoir though microdroplet forming device into a stirred ionic bath. The specific conditions for alginate, chitosan, alginate/polyethylenimide (PEI) and carboxymethyl cellulose (CMC) are listed in Table 1.

a. Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microspheres. Several different polymer concentrations were used: 0.05–0.20 g/ml. The solution is loaded with a drug and suspended in 200 ml of vigorously stirred distilled water containing 1% (w/v) poly(vinyl alcohol) (Sigma). After 4 hours of stirring, the organic solvent evaporates from the polymer, and the resulting microspheres are washed with water and dried overnight in a lyophilizer. Microspheres with different sizes (1–1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation.

In this method, the polymer is first melted and then mixed with the solid particles of dye or drug that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns are obtained with this method. The external surfaces of spheres prepared with this technique are usually smooth and dense. This procedure is used to prepare microspheres made of polyesters and polyanhydrides. However, this method is limited to polymers with molecular weights between 1000–50,000.

c. Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microspheres from polymers with high melting points and different molecular weights. Microspheres that range between 1–300 microns can be obtained by this procedure. The external morphology of spheres produced with this technique is highly dependent on the type of polymer used.

d. Spray-Drying

In this method, the polymer is dissolved in methylene chloride (0.04 g/mL). A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration= 0.04 g/mL, inlet temperature=−24° C., outlet temperature= 13–15° C., aspirator setting=15, pump setting=10 mL/minute, spray flow=600 Nl/hr, and nozzle diameter=0.5 mm. Microspheres ranging between 1–10 microns are obtained with a morphology which depends on the type of polymer used. This method is primarily used for preparing microspheres designed to improve imaging of the intestinal tract, since for this application, particle size should not exceed 10μ.

e. Hydrogel Microspheres.

Microspheres made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100–170 RPM) ionic hardening bath is positioned below the extruding device to catch the forming microdroplets. The microspheres are left to incubate in the bath for twenty to thirty minutes in order to allow sufficient time for gelation to occur. Microsphere particle size is controlled by using various size extruders or varying either the nitrogen gas or polymer solution flow rates. Table 1 summarizes the various hydrogels, the concentrations, and the ionic baths that were used to manufacturing the microspheres.

TABLE 1

Hydrogel Fabrication:

| Hydrogel Bath Stirring | Hydrogel Stirring Concentration (w/v) | Solution pH (w/v) | Solution Temp. ° C. | Bath Composition | Conc. | Rate |
|---|---|---|---|---|---|---|
| Chitosan | 1.0% | 5.0 | 23° | Tripolyphosphate | 3.0% | 170 RPM |
| Alginate | 2.0% | 7.4 | 50° | Calcium Chloride | 1.3% | 160 RPM |
| Alginate/PEI | 2.0/6.0% | 7.4 | 50° | Calcium Chloride | 1.3% | 160 RPM |
| CMC | 2.0% | 7.4 | 50° | Lead Nitrate | 10.0% | 100 RPM |

Chitosan microspheres can be prepared by dissolving the polymer in acidic solution and crosslinking it with tripolyphosphate. Carboxymethyl cellulose (CMC) microspheres were prepared by dissolving the polymer in acid solution and precipitating the microsphere with lead ions. Alginate/polyethylene imide (PEI) were prepared in order to reduce the amount of carboxylic groups on the alginate microcapsule. The advantage of these systems is the ability to further modify their surface properties by the use of different chemistries. In the case of negatively charged polymers (e.g., alginate, CMC), positively charged ligands (e.g., polylysine, polyethyleneimine) of different molecular weights can be ionically attached.

Materials That Can be Incorporated into the Microspheres.

The preferred materials to be incorporated into the bio-adhesive particles are drugs and imaging agents. The drugs which are most advantageous to incorporate include antibiotics, antivirals (especially protease inhibitors alone or in combination with nucleosides for treatment of HIV or Hepatitis B or C), anti-parasites (helminths, protozoans), anti-cancer (referred to herein as "chemotherapeutics", including cytotoxic drugs such as cisplatin and carboplatin, BCNU, 5FU, methotrexate, adriamycin, camptothecin, and taxol), antibodies and bioactive fragments thereof (including humanized, single chain, and chimeric antibodies), antigen and vaccine formulations, peptide drugs, anti-inflammatories, and oligonucleotide drugs (including antisense, aptamers, ribozymes, external guide sequences for ribonuclease P, and triplex forming agents). Preferred drugs are those which are approved for systemic administration by injection (intravenous, subcutaneous, percutaneous) which do not have sufficient bioavailability when administered orally, nasally, vaginally or rectally, or to the pulmonary system to be clinically effective. The bioavailability of these drugs by these routes is substantially improved by administration in the bioadhesive formulations disclosed herein.

Examples of other useful drugs include ulcer treatments such as Carafate™ from Marion Pharmaceuticals, neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Testred (methyltestosterone) from ICN Pharmaceuticals, and antiparasitics such as mebendzole (Vermox™, Jannsen Pharmaceutical). Other drugs for application to the vaginal lining or other mucosal membrane lined orifices such as the rectum include spermacides, yeast or trichomonas treatments and anti-hemorrhoidal treatments.

Antigens can be microencapsulated in one or more types of bioadhesive polymer to provide a vaccine. The vaccines can be produced to have different retention times in the gastrointestinal tract. The different retention times, among other factors, can stimulate production of more than one type (IgG, IgM, IgA, IgE, etc.) of antibody.

In a preferred method for imaging, the radio-opaque material such as barium is coated with polymer. Other radioactive materials or magnetic materials could be used in place or, or in addition to, the radio-opaque materials. Examples of other materials include gases or gas emitting compounds, which are radioopaque.

Administration of Bioadhesive Microspheres to Patients.

The microspheres are administered in suspension or in ointment to the mucosal membranes, via the nose, mouth, rectum, or vagina. Pharmaceutically acceptable carriers for oral or topical administration are known and determined based on compatibility with the polymeric material. Other carriers include bulking agents such as Metamucil™.

These microspheres are especially useful for treatment of inflammatory bowel diseases such as ulcerative colitis and Crohn's disease. In ulcerative colitis, inflammation is restricted to the colon, whereas in Crohn's disease, inflammatory lesions may be found throughout the gastrointestinal tract, from the mouth to the rectum. Sulfasalazine is one of the drugs that is used for treatment of the above diseases. Sulfasalazine is cleaved by bacteria within the colon to sulfapyridine, an antibiotic, and to 5-amino salicylic acid, an anti-inflammatory agent. The 5-amino salicylic acid is the active drug and it is needed locally. Direct administration of the degradation product (5-amino salicylic acid) may be more beneficial. A bioadhesive drug delivery system could improve the therapy by retaining the drug for a prolonged time in the intestinal tract. For Crohn's disease, retention of 5-aminosalicylic acid in the upper intestine is of great importance, since bacteria cleave the sulfasalazin in the colon, the only way to treat inflammations in the upper intestine is by local administration of 5-aminosalicylic acid.

Gastrointestinal Imaging.

Barium sulfate suspension is the universal contrast medium used for examination of the upper gastrointestinal tract, as described by D. Sutton, Editor, *A Textbook of Radiology and Imaging*, Volume 2, Churchill Livingstone, London (1980), even though it has undesirable properties, such as unpalatability and a tendency to precipitate out of solution.

Several properties are critical: (a) Particle size: the rate of sedimentation is proportional to particle size (i.e., the finer the particle, the more stable the suspension); (b) Non-ionic medium: charges on the barium sulfate particles influence the rate of aggregation of the particles, and aggregation is enhanced in the presence of the gastric contents; and (c) Solution pH: suspension stability is best at pH 5.3, however, as the suspension passes through the stomach, it is inevitably acidified and tends to precipitate.

The encapsulation of barium sulfate in microspheres of appropriate size provides a good separation of individual contrast elements and may, if the polymer displays bioadhesive properties, help in coating, preferentially, the gastric mucosa in the presence of excessive gastric fluid. With bioadhesiveness targeted to more distal segments of the gastrointestinal tract, it may also provide a kind of wall imaging not easily obtained otherwise.

The double contrast technique, which utilizes both gas and barium sulfate to enhance the imaging process, especially requires a proper coating of the mucosal surface. To achieve a double contrast, air or carbon dioxide must be introduced into the patient's gastrointestinal tract. This is typically achieved via a nasogastric tube to provoke a controlled degree of gastric distension. Studies indicate that comparable results may be obtained by the release of individual gas bubbles in a large number of individual adhesive microspheres and that this imaging process may apply to intestinal segments beyond the stomach.

An in vivo method for evaluating bioadhesion uses encapsulation of a radio-opaque material, such as barium sulfate, or both a radio-opaque material and a gas-evolving agent, such as sodium carbonate, within a bioadhesive polymer. After oral administration of this radio-opaque material, its distribution in the gastric and intestinal areas is examined using image analysis.

The present invention will be further understood by reference to the following non-limiting examples.

EXAMPLE 1

Evaluation of Bioadhesive properties of Polymeric Microspheres.

Polymers were evaluated for their bioadhesive potential using microspheres with diameters ranging from 700–800 $\mu$m and 700–2400 $\mu$m for the thermoplastics and hydrogels, respectively. The tensile type experiment used in this study offers several advantages over previous techniques. The setup enables one to determine bioadhesive forces between a single microsphere and intestinal mucosa. Since the experiment was conducted in an aqueous environment, problems in distinguishing between surface tension forces at the air/liquid interface and forces at the microsphere/mucus interface were eliminated.

The results, shown in FIGS. 3a, 3b, 3c and 3d, demonstrate that polymers with higher concentrations of carboxylic acid groups such as alginate and polyanhydrides, produce greater bioadhesive bonds. The extremely high forces obtained for poly(fumaric-co-sebacic) anhydride (20:80) (50 mN/cm$^2$) indicate that bioerodible polymers are very promising bioadhesive delivery systems.

The results also indicate that different fabrication methods which result in different morphologies exhibit different bioadhesive forces (e.g., PLA microspheres made by solvent evaporation adhere much stronger than PLA microspheres made by hot-melt microencapsulation). Comparison of the adhesive forces for polycarbophile, which was found to have good bioadhesive properties, show that polycarbophile displays bioadhesive forces of 1061 dyne/cm$^2$ (106.1 N/M$^2$ or 10.61 mN/cm$^2$) while most of the polymers described herein exhibit forces that range between 100 to 400 N/m$^2$.

Figure 3A:
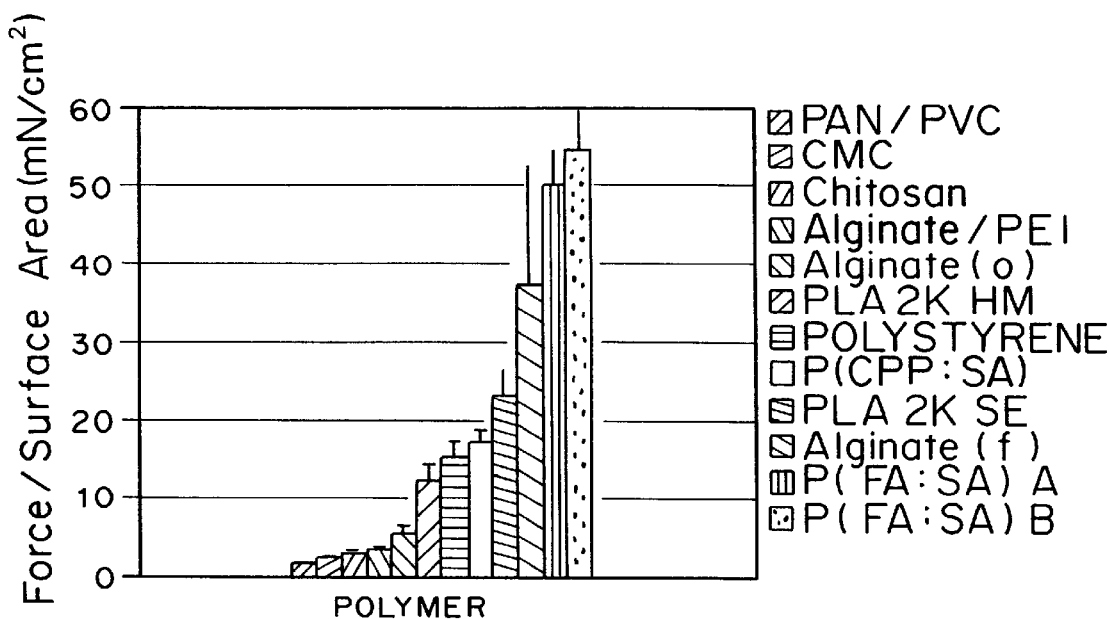
FIG. 3a is a graph of force of detachment per projected surface area (mN/cm$^2$) for various polymers. The polymers used in this study included the following: alginate (one sample prepared several hours prior to testing (alginate (f)) (diameter of approximately 700$\mu$) and another prepared several months prior to testing and left in a Ca$^+$ solution (alginate (o)) (diameter of approximately 2400 $\mu$), alginate/polyethylene imide (alginate/PEI) (diameter of approximately 2100$\mu$), carboxymethylcellulose (CMC) (diameter of approximately 1800$\mu$), chitosan (high molecular weight) (diameter of approximately 2000$\mu$), polyacrylonitrile/polyvinyl chloride (PAN/PVC) (diameter of approximately 2900$\mu$), polylactic acid: MW=2,000 (one sample made by the hot melt technique (PLA 2K HM) (diameter of approximately 780$\mu$)) and one sample made by the solvent evaporation technique (PLA 2K SE) (diameter of approximately 800$\mu$)), polystyrene (diameter of approximately 800$\mu$), poly[bis(p-carboxy phenoxy) propane-co-sebacic anhydride] made with sudan red dye (P(CPP:SA)) (diameter of approximately 780$\mu$), and poly[fumaric-co-sebacic anhydride] (one sample made with acid orange dye (P(FA:SA)A) (diameter of approximately 780$\mu$) and one sample containing no dye (P(FA:SA) B (diameter of approximately 780$\mu$). The forces were measured as the weight (mg) required to remove the microsphere from the intestinal tissue after a seven minute adhesion time using the Cahn electrobalance and converted to units of force (mN). These forces were then normalized by dividing by the surface area in contact with the tissue for each case. The surface areas were determined by the projection of the spherical cap of the microsphere that penetrated below the surface level of the tissue (Area=$\pi R^2 - \pi (R-a)^2$, where 'R' is the microsphere radius and 'a' is the depth of penetration). All force/surface area values are presented with the standard errors of measure (SEM).
Figure 3B:
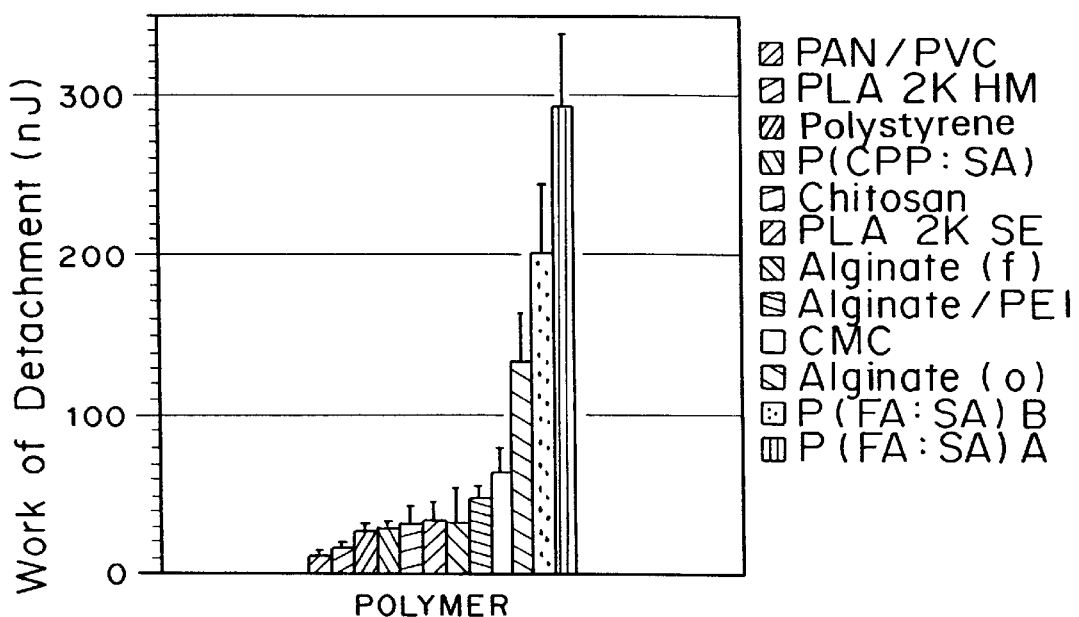
FIG. 3b is a graph of the work of detachment (nJ) for the polymeric microspheres described in FIG. 3a. Work values were determined from the areas beneath the curves of the force versus distance graphs produced with the Cahn electrobalance, and are presented with standard errors of measure.
Figure 3C:
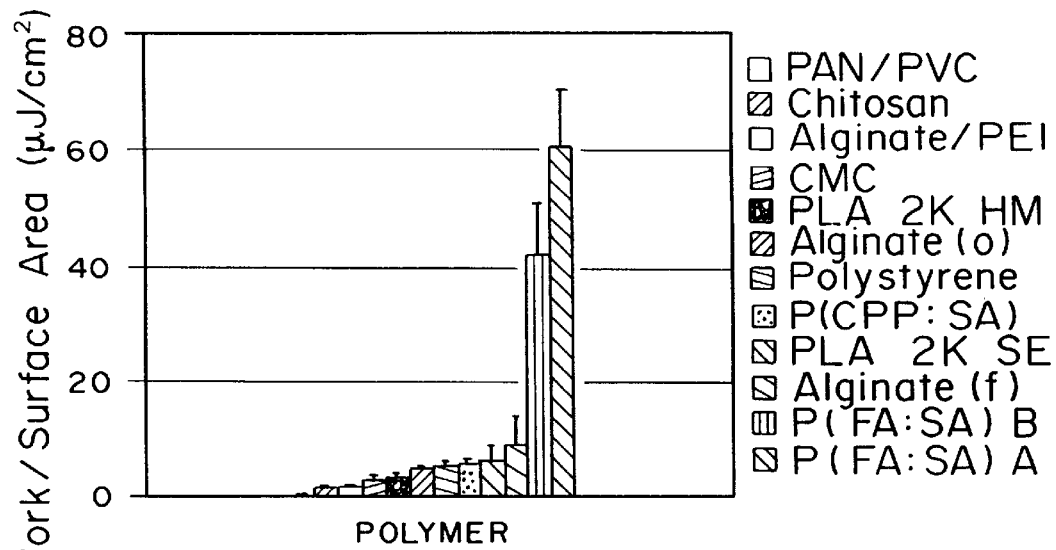
FIG. 3c is a graph of work of detachment per projected surface area ($\mu$J/cm$^2$) for the polymeric microspheres described in FIG. 3a. All work/surface area values are presented with the standard errors of measure.
Figure 3D:
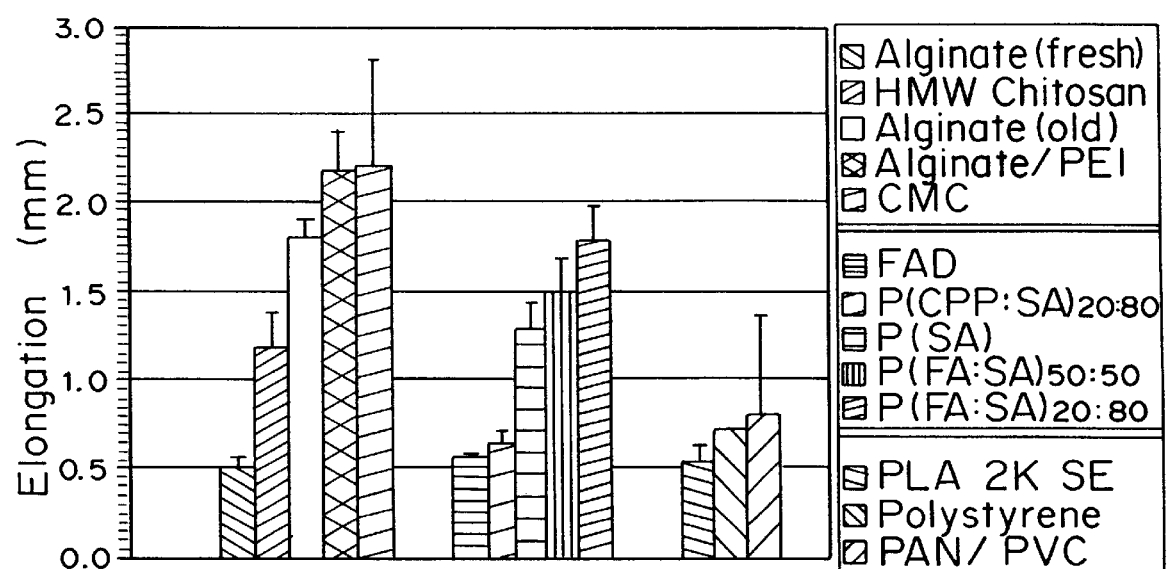
FIG. 3d is a graph of the evaluation of tissue elongation (mm) for microspheres made of the polymers listed in FIG. 3a, as well as oleic acid dimer (FAD) and polysebacic acid (P(SA)) (average diameters of approximately 780$\mu$).
Figure 4A:
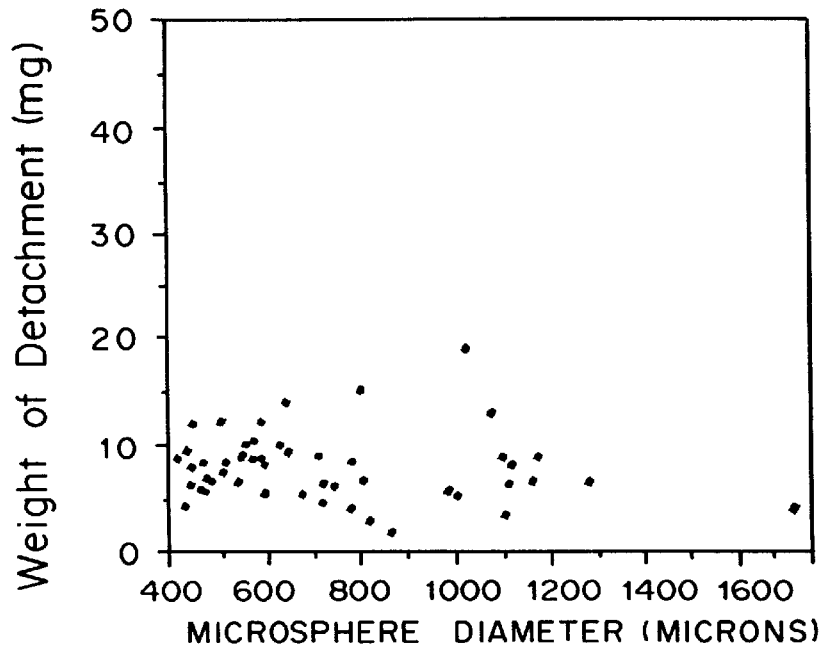
FIG. 4a is a graph of the weight of detachment versus microsphere diameter. The microspheres in this study were poly[bis(p-carboxy phenoxy) propane-co-sebacic anhydride] made with Sudan red dye made by the hot melt technique. The microsphere diameters were measured with a micrometer prior to testing. The weight of detachment is the weight, measured by the Cahn electrobalance, which is required to remove the microsphere from the intestinal tissue after a seven minute adhesion time.
Figure 4B:
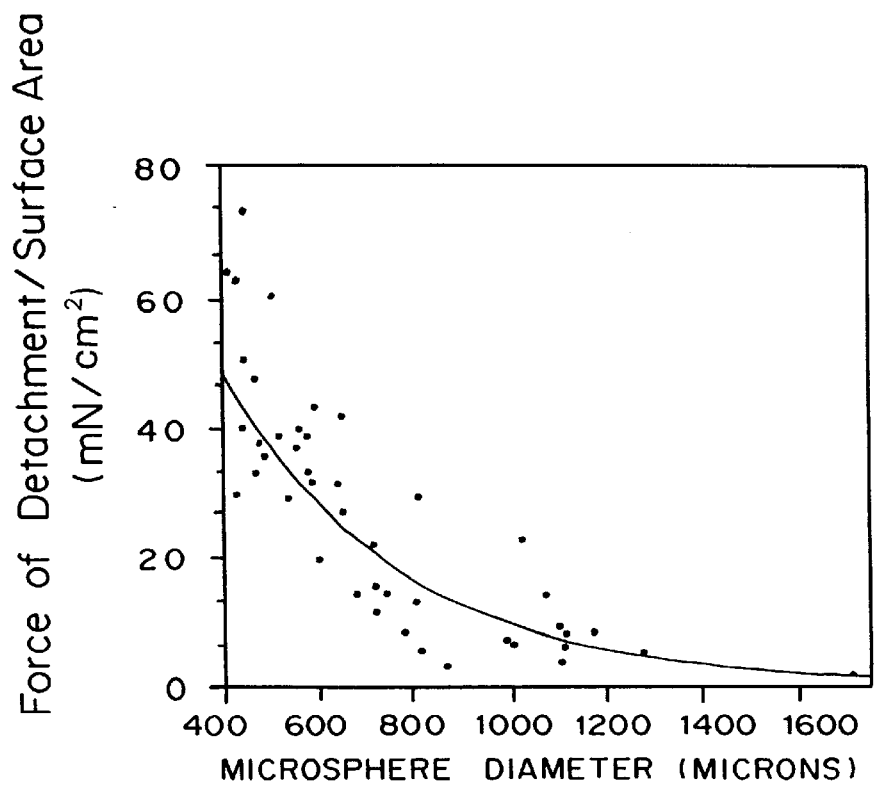
Figure 5A:
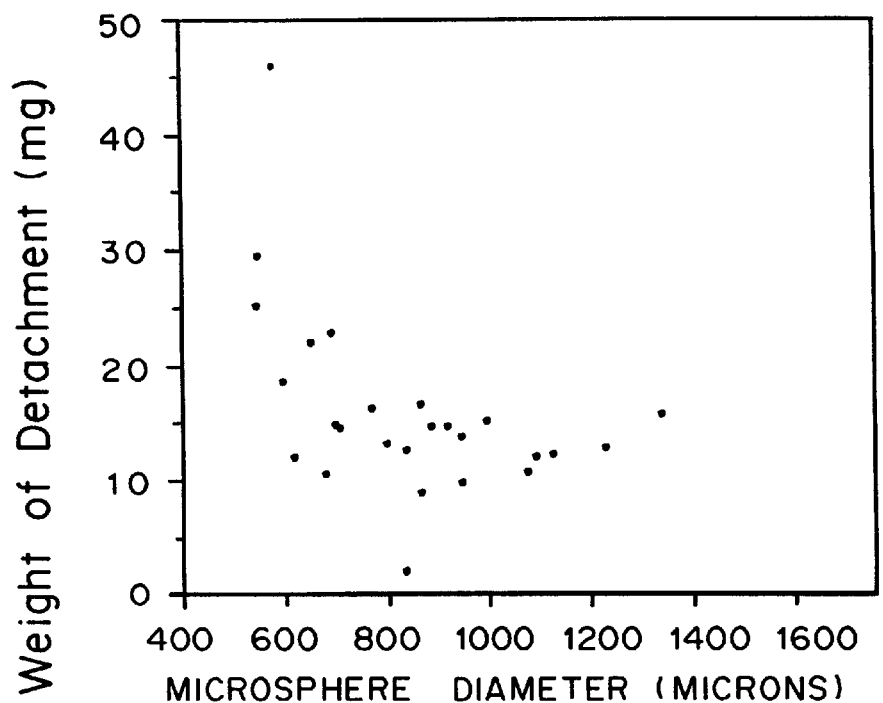
FIG. 5a is a graph of the weight of detachment (mg) versus microsphere diameter (microns) for poly[fumaric-co-sebacic anhydride] (p(FA:SA)) made by the hot melt technique. The microsphere diameters were measured with a micrometer prior to testing. The weight of detachment is the weight, measured by the Cahn electrobalance, which is required to remove the microsphere from the intestinal tissue after a seven minute adhesion time.
Figure 5B:
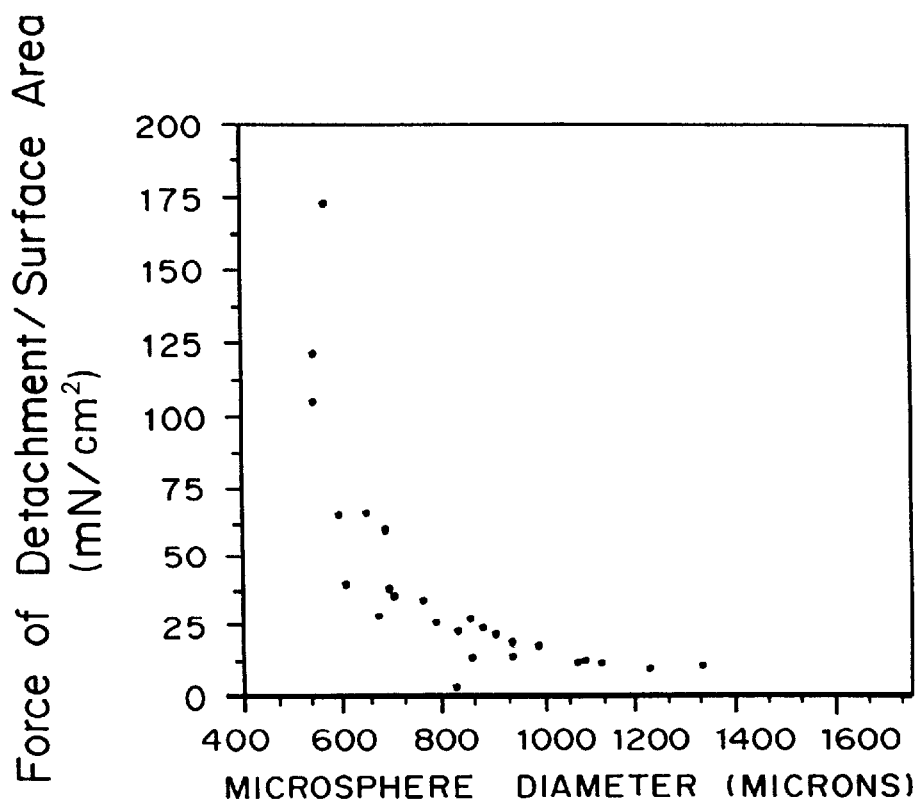

Evaluation of tissue elongations for various polymers, as shown in FIG. 3d, also shows that most hydrogels, and the most strongly adhesive thermoplastics showed long elongation numbers.

EXAMPLE 2

Effect of Microsphere Diameter on Bioadhesive Forces.

The effect of microsphere diameter on bioadhesive forces was investigated using P(CPP:SA) (20:80) and P(FA:SA) (20:80) microspheres ranging in size from 400 $\mu$m to 1700 $\mu$m, using the method described above.

The results are shown in FIGS. 4a, 4b, 5a, and 5b. There was no decline in adhesive force with a decrease in microsphere diameter. To the contrary, the forces measured increase sharply as the diameters dropped below 750 $\mu$m to at least as low as 400 $\mu$m.

EXAMPLE 3

In Vivo Transit Time Studies Using X-ray Imaging of Non-releasing Microspheres.

Microspheres were loaded with barium sulfate to render them radio-opaque. Sprague Dawley rats were anaesthetized and force-fed either a slurry of 100 mg of microspheres suspended in 2 ml of water or as controls, a pure barium sulfate suspension in distilled water. The animals were then housed in metabolic cages and the feces were collected every three hours for a period of four days. At given time intervals, the rats were X-rayed, and the distribution of the microspheres in the stomach and in the intestine was followed. The collected feces were also X-rayed in order to monitor the total transit time of the microspheres through the GI tract.

Figure 6A:
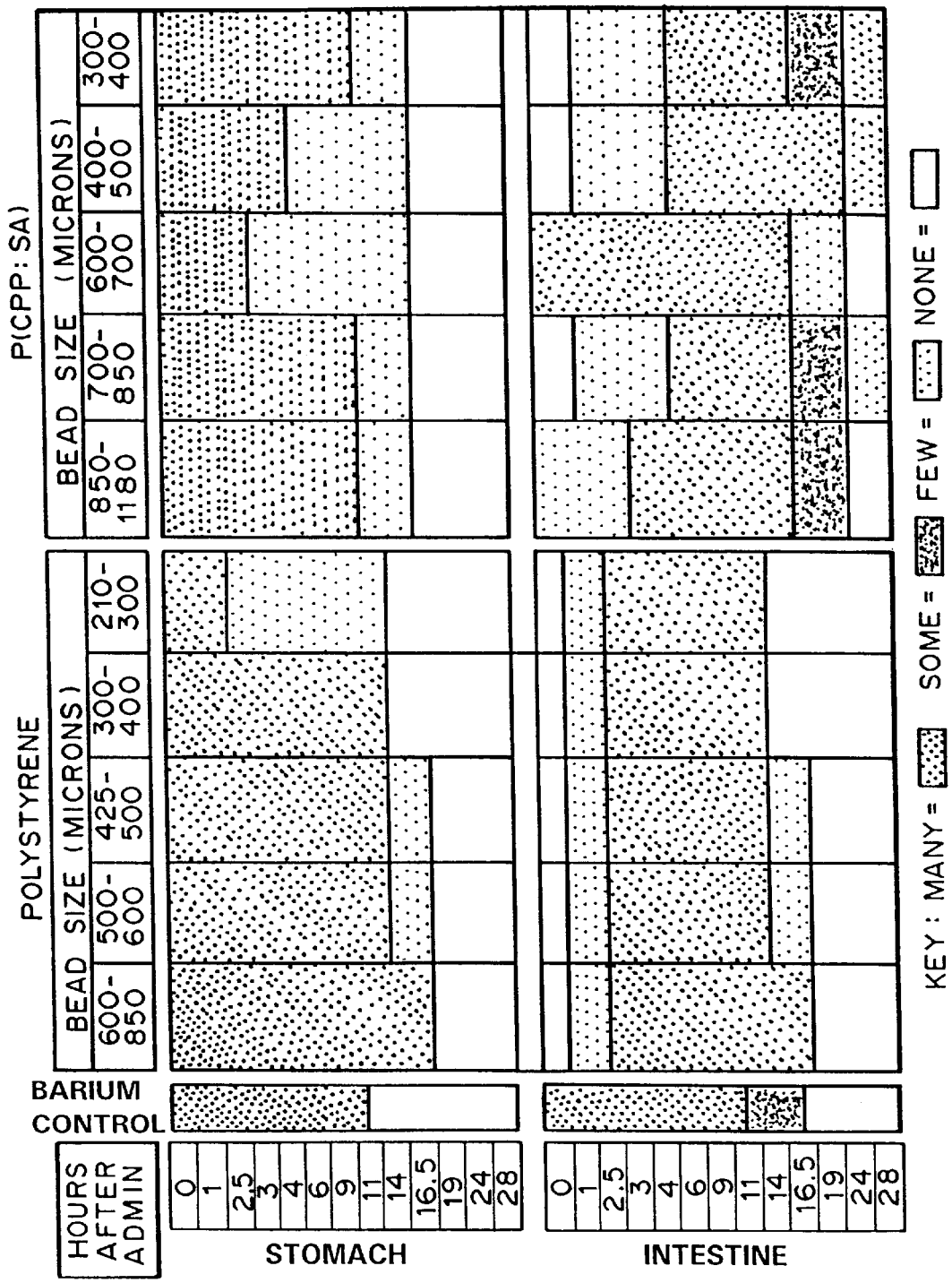
FIG. 6a is a graph of intestinal and stomach transit time (hours) for barium, polystyrene and P(CPP:SA) as a function of bead size (microns) in Sprague-Dawley rats.
Figure 6C:
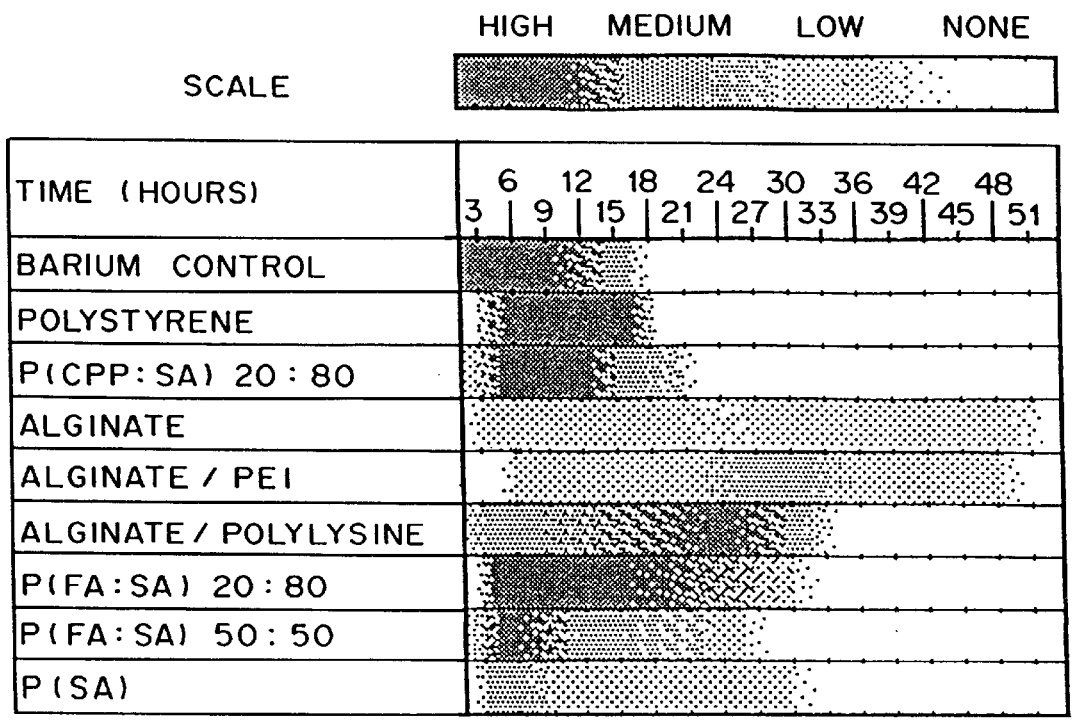
FIG. 6c is the retention time of the microspheires in the intestinal tract of Sprague-Dawley rats.
Figure 6B:
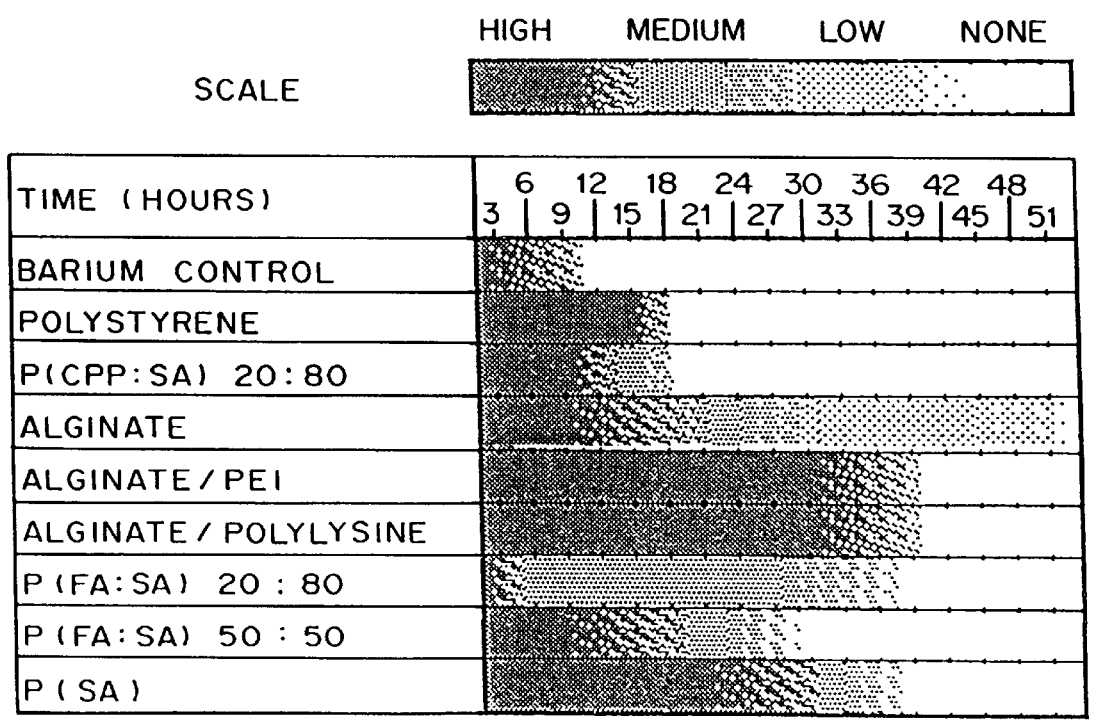
FIG. 6b is the retention time (hours) of the microspheres in the stomach of Sprague-Dawley rats.

FIGS. 6a, 6b, and 6c summarize microsphere transit times. Tests were conducted in areas of distinct pH and physiology: the stomach (low pH range), and the intestine (basic environment, pH ranging from 5–7, in the proximal to distal regions, respectively), FIGS. 6a, 6b, and 6c.

The data showed that unencapsulated barium sulfate was cleared from the stomach after 9 hours, barium sulfate encapsulated in polystyrene and P(CPP:SA) (20:80) was cleared after 18 hours while barium sulfate encapsulated in P(FA:SA) (20:80), P(FA:SA) (50:50) or PSA was not cleared until after 35 hours. At this low pH, all microspheres are neutral but long retention times were still obtained. Some alginate microspheres (diameter less than 600 microns) were retained in the stomach for over 48 hours. Alginate displayed the longest retention time in the stomach (48 hours).

Similar results were obtained for the intestine; while the alginate microspheres displayed the longest retention time from the group of hydrogels, the microspheres formed of bioerodible polymers such as P(FA:SA) (20:80) and (50:50) also had long retention times (30 hours). At these pH ranges (7.5–8.0), the thermoplastic polymers are negatively charged, which would enhance bioadhesiveness of the polymers. The in vivo results with polyanhydrides and hydrogels suggest that bioadhesion of the microspheres delays their passage through the gastrointestinal system. These results correlated with the in vitro data.

It is apparent that the smaller microspheres tend to have a longer retention time in the intestine based on the results shown in FIG. 6a. Comparing these results to those in the literature, for example, Ch'ng, H. S., H. Park, P. Kelly, and J. R. Robinson, *J. Pharm. Sci.* 74:399–405, reveals that polycarbophiles with adhesive forces of 106 N/m$^2$ are retained 24 hour in the GI tract. Adhesive forces of about 200 N/m$^2$ yielded a retention time of 28 hour.

Using scanning electron microscopy (S.E.M.), further analysis showed that the microspheres did attach to the surface of the intestine. In a typical experiment, five rats were fed with polyanhydride microspheres made of poly[bis (p-carboxy phenoxy) propane-co-sebacic] (P[CPP:SA]) (20:80). The size of the microspheres varied from 300 to 400 microns. 100 mg of spheres were suspended in 2 ml of distilled water and introduced into the stomach using a Gavage needle (gauge 16). Five hours after feeding, the rats were sacrificed and their intestines were examined to determine the distribution of microspheres through the G.I. tract. Microspheres were found in the intestine, some sticking to the food, others adhering to the tissue. The areas with spheres adhering to the tissue were washed with saline, fixed with modified "Karnofsky's" fixative, dehydrated with a graded series of ethanols, and critical-point dried. Samples were sputter-coated with gold and examined with S.E.M. A typical example of microspheres adhering to the intestine wall is shown in FIG. 8.

EXAMPLE 4
Preparation of Polyacrylamide Microspheres with High Bioadhesive Forces.

Preparation of Microspheres.

Polyacrylamide microspheres were produced by polymerizing an aqueous emulsion of acrylamide and bis methacrylamide in hexane. The following stock solutions were used:
1. 30% acrylamide (w/v), 10% bismethylacrylamide (w/v) in distilled water. The stock solution was treated with mixed bed ion-exchange resins to remove acrylic acid normally found in commercial preparations.
2. 1.2 M Tris pH 7.7.
3. 40% ammonium persulfate (w/v)
4. TEMED (N,N,N',N'-Tetramethylethylenediamine)

2 ml of the acrylamide stock, 1 ml of Tris stock, 0.1 ml of ammonium persulfate and 2 ml of distilled water to make a final volume of 5.1 ml of 12% acrylamide/4% bis methylacrylamide solution. This working solution was extensively degassed under water vacuum to remove dissolved oxygen which might inhibit the polymerization reaction.

The acrylamide solution was added dropwise to 300 ml of n-hexane which was stirred at a rate of about 500 rpm with an overhead stirrer. Approximately 0.25 ml of SPAN 85 was added to the solution to prevent aggregation of the emulsion droplets. The stirring was generally maintained for 1–2 minutes until the emulsion reached the approximate desired size. To initiate polymerization, 1 ml of TEMED was added to the n-hexane phase and stirring was continued for 30 minute. The beads were harvested and separated according to size by passing the solution through a series of graded sieves. Spheres having a diameter of between 300 and 800 μM were selected for further studies.

EXAMPLE 5
Surface Activation of the Polyacrylamide Microspheres.

Polyacrylamide microspheres were treated with carbonyldiimidazole (CDI) to covalently attach cation agents such as polyethyleneimine or polylysine. Typically one half-batch of the polyacrylamide beads were incubated with 0.5 M sodium carbonate for 1 hour at 60° C. with shaking. The sodium carbonate solution was changed twice with fresh solution during the incubation. This procedure is thought to hydrolyze the beads and produce free carboxyl groups which might be available for CDI reaction.

Next the beads were solvent-exchanged with two changes of dry acetone and then incubated with 4.0% CDI (w/v) in acetone for 1 hour at 25° C. The incubation was repeated for an additional hour with fresh CDI solution. The beads were then washed twice with acetone to remove unbound CDI and then incubated with 10% polyethyleneimine (w/v), MW 1800) or else 1% poly-1-lysine in 0.2 M sodium borate buffer, pH 9.0 at 4° C. for 24 hours. The beads were washed twice with borate buffer and stored in 2 M ammonium chloride until needed. The ammonium chloride was used to inactivate "free" CDI binding sites. The beads were washed three times with 10 mM Tris, pH 7.0 immediately before use.

Microspheres can be tested by the "Sprinkle Test" as follows. Microspheres are sprinkled over excised intestinal tissue segments. These segments were then placed in a buffer solution and left to incubate at 4° C. on a slowly moving shaker for 30 minutes. The samples were then analyzed with a stereo microscope. Typical results are shown in Table 2 along with corresponding force measurements derived from the Cahn microbalance, for microspheres of similar size (between 710–850 μm).

TABLE 2

Adhesive forces for various polymers.

| POLYMER | COATING | CAHN FORCE |
|---|---|---|
| p (FA:SA) | well coated | app. 26 mg |
| polyacrylamide | | app. 10 mg |
| CDI/Polyacrylamide | well coated | app. 20 mg |
| p (CPP:SA) | scattered | app. 8 mg |

EXAMPLE 6
Comparative In Vitro Test of Bead Attachment to Rat Intestine.

Another way of comparing the relative bioadhesion capabilities of the microspheres was to incubate the different polymer particles with isolated rat intestine under physiological conditions. Typically, the jejunum from a newly sacrificed rat was removed, flushed with about 10 ml of DPBS, inverted on a stainless steel rod and divided into segments for testing. The segments were fashioned into sacs by attaching sutures to the cut ends and then filling with DPBS. The intestinal sacs were then incubated with a known number of microspheres of defined size range for a period of 30 minute at 4° C. at shaking rate of about 30 r.p.m. At the end of the test period, the number of beads that attached to the intestine were counted as well as the number of unattached microspheres. See Table 3.

TABLE 3

Bioadhesiveness of Microspheres to rat intestine.

| Polymer | Attached | Unattached | Total | % Binding | Sac Length cm | Beads bound per cm sac |
|---|---|---|---|---|---|---|
| P (CPP:SA) | 24 | 261 | 285 | 8.4 | 3.0 | 8 |
| P (FA:SA) | 53 | 10 | 63 | 84.1 | 4.8 | 11 |
| Acrylamide | 113 | 220 | 330 | 33.9 | 2.8 | 40 |
| CDI-Acryl | 243 | 406 | 649 | 37.4 | 4.1 | 59 |

EXAMPLE 8

Surface Activation of Hydrogel Microspheres with CDI Chemistry and Coupling of Lectin to Increase Bioadhesiveness.

A solution of 2% alginate (w/v) containing 50% Tonopaque™ (Lafayette Pharmaceuticals, Lafayette, Ind.) contrasting medium (w/v) was used to prepare alginate beads using the extrusion method described above. The beads were "hardened" for one hour in a bath of 1.3% $CaCl_2$ (w/v). The beads were then wet-sieved and only those in the size-range of 500–800 microns were used. Typically, 50 to 1000 beads are used for each experiment.

The surface hydroxyl groups of the alginate beads were activated using CDI (carbonyldiimidazole) chemistry. Briefly, the beads were solvent-exchanged by soaking in 5 volumes of anhydrous acetone for a total of 5 changes. Next, the beads were incubated in 10 mL of anhydrous acetone containing 0.4 gm of CDI (4.0% w/v) for 24 hours at 20° C. with shaking. The CDI solution was discarded and the beads were washed several times with anhydrous acetone to remove unbound CDI.

Lectin from Ulex Europaeus (UEA-I, M.W. 63,000), with high affinity to the terminal alpha-L-fucose residues of mucin in the gastrointestinal tract, was coupled to the activated alginate beads. The activated beads were resuspended in 2 mL of 0.2 M sodium borate buffer, pH 9.5, to which 0.4 mg of UEA-1 lectin (Vector Laboratories, Burlingame, Calif.) was added. The beads were incubated in the lectin solution for at least 24 hours at room temperature with shaking. The beads were washed several times in the borate buffer to remove unbound lectin and incubated for 1 hour in 0.5% glycine (w/v) in borate buffer to "quench" activated sites to which lectin was not bound.

When UEA-1 alginate beads were incubated with everted rat small intestine in Hanks buffer, nearly 100% of the beads attached to the mucosa/mucin layer within 5 minute and remained firmly bound for at least 3 hours. This type of surface modification could be used on any type of bead containing surface carboxyl or hydroxyl groups to improve bioadhesion.

Lectin coated microspheres were also fabricated by first modifying the alginate and then preparing microspheres. For large scale applications, it is desirable to pretreat alginate before making microspheres with the extrusion device. In one experiment, 0.5 gm of alginate powder was treated with 0.2 gm of CDI in anhydrous DMSO (alginate is not soluble in DMSO), for 48 hours at room temperature. Next, the activated alginate was washed with excess DMSO to remove unreacted CDI and 10 mL of 0.2 M Borate buffer, pH 9.5 containing 0.5 mg of UEA-1-biotinylated lectin was added to the powder. The ligand coupling step was allowed to continue for 24 hours at 4° C. Unbound lectin was removed from the swollen powder by careful washing with borate buffer. The treated alginate was washed with distilled water and dissolved in water to make a 2% alginate solution (w/v).

This alginate solution was then used to make microspheres by extrusion into a 1.3% calcium chloride bath. The final beads displayed excellent bioadhesion to everted intestinal sacs in vitro.

The presence of biotinylated lectin on the final beads was confirmed by incubation with a commercially available, Vector stain-horseradish peroxidase (HRP) kit. The vector stain makes use of an avidin-biotin-HRP complex which binds to the biotinylated lectin attached to the beads. The peroxidase activity was visualized by a reaction with diaminobenzidine and hydrogen peroxide. This reaction caused the initially white microspheres to turn dark brown, thus confirming the presence of lectin.

EXAMPLE 9

Coating Drugs with Poly(Fumaric-co-sebacic Anhydride) to Improve Bioadhesion.

Untreated Dexatrim™ and Contac™ were first tensile tested for adhesion on freshly excised rat small intestine, under physiologic conditions, using a modified Cahn electrobalance (Model DCA 322). The materials were then dip coated with poly(fumaric-co-sebacic anhydride) in a 20:80 ratio (P(FA:SA) 20:80) dissolved in methylene chloride. After coating, the same tensile tests were repeated. The results shown in Table 3 clearly showed a marked improvement in the adhesive bond of the coated versus uncoated samples in both cases.

TABLE 4

Tensile Strength of Adhesive Bond Formed by Microspheres.

| MATERIAL | UNCOATED (mg) | COATED (mg) | INCREASE |
|---|---|---|---|
| DEXATRIM ™ | 5.00 | 31.65 | 533 |
| CONTAC ™ | 5.63 | 21.37 | 280 |

Properties such as tissue elongation and work of detachment have a strong correlation with the degree of bioadhesiveness. The average tissue elongation of Contac™ increased from 0.948 mm to 1.227 mm (29% increase) and the average work of detachment increased from 26.46 nJ to 144.14 nJ (445%) increase) with coating.

EXAMPLE 10

Binding of FA:SA Microspheres to Sheep Intestine.

In order to evaluate the importance of species differences with respect to bioadhesion, the binding of p(FA:SA) (50:50) microspheres to intestine from newly sacrificed sheep was tested. The p(FA:SA) microspheres were used because they consistently showed the highest forces of any microspheres tested with the Cahn microbalance apparatus.

Jejunum was removed from an unfasted animal immediately following sacrifice by injection of euthanasia solution and the gut was placed into chilled Dulbecco's PBS (DPBS). Two experiments were performed on this tissue: CAHN force measurements and microsphere incubation studies.

For the CAHN experiments, segments of the sheep jejunum (1 cm×1 cm) were cut and placed in DPBS in the CAHN tissue chamber. Three p(FA:SA) (20:80) microspheres, with diameters between 600–750 $\mu$, were tested using a seven minute adhesion time. The results of the experiments are shown in Table 5 as follows:

TABLE 5

Bioadhesion of p (FA:SA) (50:50) microspheres to sheep intestine

| Parameter | Averages |
| --- | --- |
| diameter ($\mu$) | 682 |
| measured force (mg) | 199.87 |
| penetration (mm) | 0.540 |
| elongation (mm) | 2.335 |
| fracture strength (mN/cm$^2$) | 545.97 |
| work of adhesion (mJ) | 30.80 |
| work of detachment (mJ) | 1,911.00 |

The interactions measured using the sheep intestine were substantially greater than those measured using rat intestine. For example, the bioadhesive fracture strength was 10 times larger than the bioadhesive fracture strength measured between rat tissue and p(FA:SA). Also the work done in separating the samples (i.e., the work of detachment) was far greater than any that had been previously recorded. Furthermore, these values (fracture strength and work) may have been even larger, but could not be recorded to the fact that the microbalance reached its home position prior to complete separation.

The bioadhesion appeared to be mainly due to interaction of the microspheres with the mucus layer. It was observed that the protective mucous coating in the sheep intestine was much thicker than that observed in the rat. These differences may be due to diet; sheep are herbivorous while rats are omnivorous, as are humans.

For the incubation study, the intestine was cut longitudinally and a 4 cm length was pinned to a piece of dental wax in a Petri dish. The gut was lightly washed with chilled saline to remove the luminal contents, but no attempt was made to wash away the extensive mucus layer that covered the mucosal surface. Several hundred beads, ranging from 300 to 500 microns in diameter, were sprinkled onto the immobilized segment and incubated at 4° C. in the DPBS, pH 7.4. After 1 hr, the intestine was briefly washed by immersion in DPBS to remove loosely bound beads and the extent of microsphere binding was evaluated. AT least 80% of the beads remained attached to the intestine and appeared to be firmly bound.

To avoid loss of bound beads due to fixation and dehydration for histology studies, the intestinal segment was briefly washed for 5 seconds in distilled water to remove adherent buffer salts, quickly frozen in liquid nitrogen and lyophilized for S.E.M. S.E.M. of the sampled confirmed gross observations. Mucous strands completely covered every villus structure. Microspheres were engulfed in the mucus layer to at least one-half of the bead diameter in many cases and most of the spheres showed significant adsorption onto their surface. Clearly, the mucus attachment served to tightly anchor the FA:SA microspheres to the luminal surface and provide an intimate contact that should enhance drug delivery to the epithelium.

EXAMPLE 11
Binding of Microspheres to Monkey Intestine.

The jejunum was obtained from a five year old female monkey that had been on a high calorie, vegetarian diet of monkey chow and was not fasted prior to sacrifice. The tissue was kept chilled on ice in Dulbecco's phosphate buffered saline (DPBS). Segments of the tissue (1 cm×2 cm) were cut and placed in the CAHN tissue chamber for microbalance analysis. Three different thermoplastics (polyanhydrides) were analyzed for bioadhesion: p(CPP:SA) (20:80), p(FA:SA) (20:80), and p(FA:SA) (50:50). The average results are shown in Table 6 as follows:

TABLE 6

Binding of thermoplastic microspheres to monkey intestine

| Polymer: | p(CPP:SA) (20:80) | p(FA:SA) (20:80) | p(FA:SA) (50:50) |
| --- | --- | --- | --- |
| n | 1 | 5 | 3 |
| ave. diameter | 785 | 787 | 1120 |
| measured force (mg) | 7.85 | 5.1 | 23.82 |
| penetration (mm) | 0.9 | 1.0 | 0.511 |
| elongation (mm) | 2.433 | 1.12 | 3.436 |
| fracture strength (mN/cm$^2$) | 15.91 | 10.5 | 24.20 |
| work of adhesion (mJ) | 68.32 | 56.39 | 35.82 |
| work of detachment (mJ) | 82.18 | 24.46 | 500.78 |

The p(FA:SA) (50:50) microspheres appeared to display the strongest adhesion to the monkey tissue. The fracture strength was approximately half as large as that measured with rat intestinal tissue. The tissue was unique in that very little mucus was visible on the surface. Even when a strong interaction was noted, it was difficult to see the characteristic strands of mucus stretching between the bioadhesive and the living tissue. However, fairly long tissue elongations were measured compared to those which were commonly observed when analyzing the rat intestinal tissue.

The different microspheres that had been tested for bioadhesion with the CAHN microbalance were tested for bioadhesion in vitro using the "sprinkle test". The results of the incubations confirmed that only the FA:SA beads showed any significant bioadhesion, but only 20% of the initial loading of the beads remained tightly bound to the monkey intestine after 1 hr. When this experiment was performed with sheep intestine under identical conditions, fully 80% of the initial beads remained attached. The gross absence of mucus from the monkey intestine, compared to the full mucus covering of the sheep intestine suggested at least one obvious reason for the difference in bioadhesion.

By S.E.M., the morphology of the jejunum was well-preserved and the obvious absence of mucus strands was confirmed. In general, beads were bound to highly discrete locations where the mucus network was intact or else attached directly to the epithelial cells covering the villi. In some instances, beads or small groups of beads appeared to be mechanically lodged between adjacent villous structures. The findings suggest that although direct binding of the FA:SA microspheres to the absorptive epithelium does occur, the adhesion of the polymer spheres to mucus is much more vigorous and is a more important component of the bioadhesion process.

Modifications and variations of the method and bioadhesive microsphere compositions described herein will be obvious to those skilled in the art from the foregoing detailed description. Such modifications and variations are intended to come within the scope of the appended claims.

We claim:

1. A drug formulation comprising drug encapsulated within a microsphere having a polymeric surface with an adhesive force equivalent to an adhesive force of between 110 N/m$^2$ and 100,000 N/m$^2$ measured on rat intestine, wherein the drug is selected from the group consisting of antibiotics, antivirals, anti-parasites (helminths, protozoans), anti-cancer, antibodies and bioactive fragments thereof, antigen and vaccine formulations, peptide drugs, anti-inflammatories, and oligonucleotide drugs.

2. The formulation of claim 1 where in the drug does not have sufficient bioavailability when administered orally, nasally, vaginally or rectally, or to the pulmonary system to be clinically effective except when encapsulated within the microspheres.

3. The formulation of claim 1 wherein the drug is a protease inhibitors alone or in combination with nucleosides for treatment of HIV or Hepatitis B or C.

4. The formulation of claim 1 wherein the drug is a protein or peptide.

5. The formulation of claim 1 wherein the drug is selected from the group consisting of cisplatin and carboplatin, BCNU, 5FU, methotrexate, adriamycin, camptothecin, and taxol.

6. The formulation of claim 1 wherein the drug is antibodies and bioactive fragments thereof.

7. The formulation of claim 1 wherein the drug is an anti-inflammatory.

8. The formulation of claim 1 wherein the drug is selected from the group of oligonucleotide drugs consisting of antisense, aptamers, ribozymes, external guide sequences for ribonuclease P, and triplex forming agents.

9. The formulation of claim 1 wherein the polymer is selected from the group of synthetic polymers consisting of polyamides, polycarbonates, polyalkylenes, polyacrylamides, poly(hydroxy acids), polyanhydrides, polyorthoesters, blends and copolymers thereof.

10. The formulation of claim 9 wherein the polymer is a copolymer of fumaric acid and sebacic acid.

11. The formulation of claim 1 wherein the microspheres are targeted to a molecular present on a mucosal surface.

12. The formulation of claim 1 wherein the polymer is modified to increase the number of available charged groups.

13. The formulation of claim 12 wherein the charged groups are carboxyl groups.

14. The formulation of claim 12 wherein the charged groups are amino groups or polyamino groups.

15. The formulation of claim 1 wherein the polymer is modified by binding of mucin binding compounds selected from the group consisting of sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, mucoproteins, mucopolysaccharides, mucopolysaccharide-protein complexes, lectins, and antibodies immunoreactive against proteins on the mucosal surface.

16. The formulation of claim 1 wherein the polymer forms the entire microsphere.

17. The formulation of claim 1 wherein the polymer is coated onto the surface of a microsphere formed of a different material.

18. A method for delivering a drug comprising administering to a mucosal surface a drug formulation comprising drug encapsulated within a microsphere having a synthetic polymeric surface with an adhesive force equivalent to an adhesive force of between 110 N/m$^2$ and 100,000 N/m$^2$ measured on rat intestine, wherein the drug is selected from the group consisting of antibiotics, antivirals, anti-parasites (helminths, protozoans), anti-cancer, antibodies and bioactive fragments thereof, antigen and vaccine formulations, peptide drugs, anti-inflammatories, imaging agents and oligonucleotide drugs, in combination with a pharmaceutical carrier.

19. The method of claim 18 wherein the microspheres are administered nasally.

20. The method of claim 18 wherein the microspheres are administered orally.

21. The method of claim 18 wherein the microspheres contain a compound detectable by imaging and are administered orally to a patient, wherein the gastrointestinal tract of the patient is imaged based on the location of the microspheres in the gastrointestinal tract.

22. The method of claim 18 wherein the microspheres include mucin binding compounds selected from the group consisting of sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, mucoproteins, mucopolysaccharides, mucopolysaccharide-protein complexes, lectins, and antibodies immunoreactive against proteins or sugar structure on the mucosal surface.

23. The method of claim 18 wherein the polymer is a copolymer of fumaric acid and sebacic acid.

* * * * *